United States Patent [19]
Shoher et al.

[11] 4,434,211
[45] Feb. 28, 1984

[54] METHOD FOR BONDING CERAMIC TO NOBLE BASED METALS AND PRODUCT

[76] Inventors: Itzhak Shoher, 50 Shlomo Hamelech St., Tel-Aviv; Aharon Whiteman, 13 I.L. Perez St., Pethah-Tikvah, both of Israel

[21] Appl. No.: 460,918

[22] Filed: Jan. 14, 1983

Related U.S. Application Data

[60] Continuation of Ser. No. 171,255, Jul. 22, 1980, abandoned, which is a division of Ser. No. 18,767, Mar. 8, 1979, abandoned.

[51] Int. Cl.³ .......................... B22F 3/00; B22F 5/00; B22F 7/00
[52] U.S. Cl. ................................. 428/552; 428/553; 75/247; 75/253; 427/2; 427/190; 427/191; 427/201; 427/203; 427/205; 427/376.4; 427/376.6; 427/380; 427/405; 427/419.1; 427/419.2
[58] Field of Search ................ 427/2, 376.2, 376.4, 427/190, 376.6, 191, 376.7, 201, 376.8, 404, 405, 419.1, 383.7, 383.9, 380, 419.2, 419.3, 419.4, 205, 203; 75/253, 0.5 R, 168, 172 R, 172 G, 173 R, 200, 201, 247; 228/122; 428/546, 552, 553

[56] References Cited

U.S. PATENT DOCUMENTS

| | | | |
|---|---|---|---|
| 2,654,945 | 10/1953 | Richardson et al. | 75/247 |
| 3,450,545 | 6/1969 | Ballard et al. | 75/0.5 R |
| 3,995,371 | 12/1976 | O'Keefe | 427/2 |
| 4,062,676 | 12/1977 | Knosp | 75/165 |
| 4,125,442 | 11/1978 | Rogers | 427/376.4 |
| 4,132,830 | 1/1979 | Tsai | 75/165 |
| 4,181,757 | 1/1980 | Youdehs | 75/165 |
| 4,240,847 | 12/1980 | Chrisman | 427/376.7 |

*Primary Examiner*—S. L. Childs

[57] ABSTRACT

A method of forming a clinically unbreakable composite structure between a noble based metal and a ceramic comprising depositing a thin layer of a bonding material including finely divided particles of a noble metal halide alone or in combination with particles of a noble metal; sintering the layer at a predetermined temperature between 1775° F. and 1975° F. and firing a ceramic over the sintered coating.

7 Claims, No Drawings

METHOD FOR BONDING CERAMIC TO NOBLE BASED METALS AND PRODUCT

This application is a continuation of application Ser. No. 171,255 filed July 22, 1980 now abandoned, which is a division of application Ser. No. 018,767, filed Mar. 8, 1979, now abandoned.

The present invention relates to a novel bonding material composition and method for forming a composite body between two members and more particularly to a bonding material composition and method for joining a ceramic material to a noble based metal and for joining noble based methods to one another.

It is conventional in the field of restorative dentistry to cover the metal framework of crowns, bridges and dentures with ceramic porcelain. The porcelain is fused to the underlying metal substructure forming the crown, bridge or denture at relatively high temperature. The metal substructure is generally of a noble based metal of predominantly gold. The porcelain ceramic is a dental porcelain composed of natural feldspar, quartz and kaolin which may include small additions of other materials such as nepheline syenite, boro silicate glasses and fluxes as well as coloring agents. Although the present invention is concerned with enhancing the bond between the porcelain ceramic and metal framework of a dental restoration and alleviating stresses between the two materials it is not to be construed as limited to the field of dentistry or to the ceramic material compositions used in dentistry. In fact, the bonding material composition and method of the present invention may be used to bond any ceramic material composition particularly a ceramic enamel including glass to any noble based metal. For purposes of the present invention a noble based metal is defined as a metal or metal alloy containing one or more noble metal constituents representing all or a relatively substantial proportion by weight of such metal or metal alloy.

The problems associated with forming a clinically successful bond between a porcelain ceramic and a metal substrate are to a large extent attributable to the different thermal contraction rates of the materials. The porcelain is fired onto the metal substrate in layers at elevated temperatures and cooled to room temperature. This tends to develop interfacial stresses between the materials. Moreover the bonded joint, particularly for noble based metal substrates, is generally attributed to mechanical retention forces and Van der Waals forces with little, if any, chemical bonding. The cohesion resulting from such a bond is invariably weaker than in a chemically formed bond. A chemical bond requires electron transfer to occur at the interface between the two members thereby forming an autogeneous joint which can be stronger than the individual connecting members.

Attempts have been made in the prior art to deposit an intermediate layer upon the metal framework before firing the ceramic porcelain in order to improve the degree of adhesion of the porcelain to the metal. One such example is the formation of an oxide such as tin oxide upon the metal surface prior to the application and firing of the porcelain coating. Although the oxide layer is chemically bonded to the metal framework it apparently does not significantly interact with the porcelain to form a chemical bond. Moreover it does not form a clinically unbreakable joint under clinical testing. It is also well-known that adhesion can be promoted by surface preparation of the metal body. The increase in adhesion following surface preparation is primarily attributable to an increase in Van der Waal forces and mechanical interlocking of the members.

The present invention is primarily concerned with the formation of a clinically unbreakable composite body between a ceramic member and a noble based metal member or between two such metal members by the incorporation of a bonding material between the members to be joined. In accordance with the preferred method of the present invention the bonding material is initially deposited upon the surface of either one or both of the members to be joined to form a relatively uniform layer which is heated to a predetermined temperature until the bonding material is sintered and substantially wetted to the member surface whereupon the two members are brought together, with the substantially sintered bonding material therebetween and the assembly baked in an oven at a second predetermined temperature sufficient to cause the bonding material to react at the interface with the overlaid member. The preliminary sintering step is preferred but not essential particularly in the case of two metal members. However, in the latter case the second heating step should be at a sufficiently elevated temperature to wet the bonding material to both members. The bonded joint formed following this procedure is practically unbreakable. In preparing fixed prosthetic dental devices the porcelain ceramic is preferably applied in layers to the metal framework surface following the steps of applying and sintering the bonding material to the metal framework. The porcelain is fired onto the sintered coated framework at a lower temperature than the sintering temperature. The bonding material may also be applied to a ceramic substrate and to the metal member separately before joining the two.

The bonding material and method of the present invention may also be used to bond a porcelain superstructure to a noble based metal foil, e.g., a platinum foil or to repair or extend a gingival margin, a hole, slice or casting defect or for use in joining a metal understructure to a foil or to join a preformed or precasted metal understructure for a pontic to a platinum foil coping or to form an understructure in which porcelain may be bonded to the whole unit. In addition to dental and medical applications the bonding agent and method is employable in a variety of different technical fields in which a ceramic material is to be joined to a metal material.

The bonding material composition is also usable as a metalizing composition for ceramic substrates in the production of printed electrical components. In such cases the bonding material composition would be applied to the surface of the ceramic at predetermined locations and sintered at a proper temperature to condition the ceramic surface at such locations for circuit printing and wire soldering. The sintered surfaces provide a highly conductive path which is bonded to the substrate to a degree heretofore unattainable. Moreover, the fired on bonding material composition of the present invention is refirable and essentially nonoxidizing.

The bonding material composition of the present invention comprises a finely divided metal particle composition comprising a halide of a noble metal in a range from about 1 to 100% by weight of the composition in combination with a noble based metal in a range from zero to 99% by weight of the composition. The preferred noble metal is selected from the group consisting of silver, palladium, platinum and gold with other noble metals such as indium, rhodium, osmium and iridium being less desirable. The halide is preferably selected from the group consisting of a chloride or fluoride, although a bromide or iodide may be used. The noble based metal component of the bonding material composition may be in any desired particulate form such as flakes, granules or powder and of a particle size between about 1 to 60 microns although a particle size of below about 10 microns is preferred. A particle size in a range of between about 1-10 microns is considered optimum for dental application. Elemental finely divided noble metal particles are commercially available or may be ground to the proper particle size in a ball mill.

The noble based metal component of the bonding material is preferably a gold based noble metal having at least about 50% by weight finely divided particles of gold with up to 45% of one or more of other finely divided noble metal particles such as silver, platinum, palladium, rhodium and indium and may contain traces of preferably no more than a total of about 5% by weight of any one or more non-precious metals such as copper, zinc, iron, tin, cadmium, magnesium, germanium, manganese, cobalt and nickel. It should be understood that the present invention is not limited to a predominantly gold based noble metal component although a predominantly gold based noble metal is preferred for dental and electronic applications because of the color and the nonoxidizing characteristic of gold.

The noble metal halide component of the composition is a critical ingredient. Elemental metallic particles of noble metals such as silver or gold will not perform the same result. It is not clear at present why the noble metal halide component alone or in combination with a noble based metal component reacts with a ceramic or noble based metal substrate upon sintering to form a clinically unbreakable bond which is believed to be chemical in nature whereas metallic noble metal particles will not. The noble metal halides are commercially available in a granulated powder or crystaline form and in a particle size range within or below the desired range for the noble based metal component. Gold chloride is commercially available as chlorauric acid (HAuCl4) in a powdered crystal form and may be directly used in this form as the gold chloride noble metal component of the present invention. The noble metal halide has been found to produce an effective bond in varying percentages by weight from as low as about one percent of the composition to 100%. For dental applications the noble metal preferably gold based component should be present in a larger proportion than that of the noble metal halide component primarily because of the desire to have a substantial background gold color underneath the porcelain ceramic overlay.

The bonding material may be used with or without a suitable binder. It is preferred, however, to suspend the bonding material in a carrying vehicle so that it may be readily and controllably applied to the surface of the metallic or ceramic member such as by brushing, painting, dipping or spraying. Any suitable carrying vehicle, preferably one which will volatilize in the sintering process without a residue, may be used including known water detergents or an organic resinous or synthetic resinous medium thinned with a suitable solvent. When a binder is not used the bonding material may be simply sprinkled over the substrate surface.

The bonding material may be deposited upon the surface of the ceramic or metal body to form a coating of any desired thickness. Moreover, the bonding material need not form a continuous layer except where electrical continuity is required. As a practical matter it is preferred to spread out the bonding material in the form of a thin film coating having a relatively uniform average thickness of less than about 0.05 mm. A substantially thicker coating will form a condensed metal mass upon sintering which is just as effective but more costly and is accordingly less desirable. In the general case, a relatively thin layer of bonding material preferably suspended in a carrier is all that is necessary.

After applying the bonding material to the surface of the metal member or to the ceramic member or to both, the bonding material is sintered to the applied member(s) at a predetermined temperature range between about 1775° F. to 1875° F. with the optimum temperature range being between about 1950° F. to 1900° F. The sintering operation may be completed within 5-25 minutes. Depending upon the noble metal halide some activation and wetting of the noble metal may occur at temperature about as low as 1600° F. In preparing a fixed prosthetic device such as a crown, bridge or denture it is preferably to select a sintering temperature which will only cause the bonding agent to form substantially spherical beads of irregular size as opposed to a continuous film. Optimum beading will occur at a temperature range between about 1800° F. to 1875° F. Thereafter, the ceramic material is fired over the sintered coating to form the composite structure. The firing temperature for the ceramic depends upon its composition but generally falls within a range of 1600°-1820° F. For metalizing applications the bonding material is deposited over a ceramic substrate and sintered at a preferred temperature range of about 1700° F. to 1720° F.

The porcelain ceramic fuses to the sintered noble based metal member to form an unbreakable joint. The sintered bonded material is believed to chemically interact with the porcelain in forming the unbreakable joint. It is not quite clear whether the noble metal chloride or fluoride itself decomposes and if so whether the evolved chlorine or fluorine completely escapes. However, the noble metal halide does contribute to the formation of an unbreakable joint. An unbreakable joint is defined for purposes of the present invention as a bonded joint which does not under clinical conditions permit separation of the members at the bonded interface. This is simply determined by applying a sufficient impact force in a direction normal to the structure until the composite structure breaks and then visably inspecting the broken structure to see if separation occurred at the interface between the members. However, it should be understood that this physical characteristic of unbreakability is not essential for many applications and, accordingly, the invention is not to be construed as requiring this degree of adhesion.

The following examples substantiate the breathe of the invention:

EXAMPLE I

A bonding material composition comprising a mixture of 98.6% by weight of finely divided particles (between 5-10 microns) of a noble based metal component having the following composition by weight: 97%

Au; 0.6% Ag; 0.4 Pt and 0.2% Pb with about 2% trace elements of Cu, Fe, Cr and Cd; and A noble metal halide of 1.4% by weight powdered silver chloride (AgCl).

The bonding composition was applied as a thin film to a noble based metal substrate of 100% platinum and sintered at a sintering temperature of 1875° F. for 3 minutes. A conventional porcelain ceramic was thereafter deposited over the sintered surface and fired at a temperature of 1775° F. The resulting structure was found to be clinically unbreakable.

Equivalent tests were conducted using other conventional dental porcelain compositions with identical results.

EXAMPLE II

Same as Example I except for different noble based substrate compositions as follows:

(a) 87.5% Au, 4.5% platinum and 6% palladium and 2% trace elements. Result—same.

(b) 52% gold, 38% palladium and 4% zinc. Result—same.

(c) 60% silver and 40% palladium. Result—same.

EXAMPLE III

Same as Example I except that the noble based metal component was reduced to 7% by weight while the silver chloride content was increased to 93%. Result—same.

EXAMPLE IV

Same as Example I except that the noble based metal component was reduced to 50% and the silver chloride content increased to 50%. Result—same.

EXAMPLE V

Bonding material composition of Example I changed as follows: Noble based metal component—93% gold, noble metal halide component—7% silver fluoride. Result—a clinically unbreakable bond.

EXAMPLE VI

Bonding material composition of Example 1 was changed to 100% platinum chloride with identical results.

EXAMPLE VII

Bonding material composition of Example I changed as follows: Noble based metal component—90% gold, Noble metal halide component—10% platinum chloride. Result—clinically unbreakable bond.

EXAMPLE VIII

Bonding material composition of Example I changed to 100% HAuCl$_4$. Result—same.

EXAMPLE IX

Bonding material composition of Example I changed to 10% HAuCl$_4$ and 90% gold. Result—clinically unbreakable bond.

EXAMPLE X

Bonding material composition of Example I changed to: Noble metal halide component; 5% AgCl, 5% PtCl, and noble based metal of 90% gold. Result—clinically unbreakable bond.

EXAMPLE XI

Bonding material composition of Example I changed to: 10% HAuCL$_4$, 5% platinum fluoride, and 80% gold. Result—same.

What is claimed is:

1. A method for forming a clinically unbreakable composite structure between a noble based metal and a ceramic comprising the steps of depositing a thin layer of a bonding material upon the surface of said noble based metal, said bonding material comprising a composition of from about one to 100% by weight of finely divided particles of a noble metal halide and from zero to 99% by weight of finely divided substantially gold based metal particles, sintering said layer of bonding material at a predetermined temperature within a temperature range between 1775° F. to 1975° F. and firing a ceramic material over said sintered coating.

2. A method as defined in claim 1 wherein said halide is a chloride.

3. A method as defined in claim 2 wherein said noble metal halide comprises a chloride of a noble metal selected from the group of noble metals consisting of platinum, palladium, gold and silver.

4. A method as defined in claim 2 wherein said sintering temperature is between about 1850° F. to 1900° F.

5. A method as defined in claim 4 wherein said unbreakable structure is a metal porcelain tooth restoration.

6. A composite structure composed of a layer of a noble based metal, a layer of ceramic material and an intermediate layer of a material having a composition of from one to 100% by weight of finely divided particles of a noble metal halide and from zero to 99% by weight of finely divided substantially gold based metal particles formed by the method of sintering said intermediate layer at a predetermined temperature range of between 1700° F. to 1975° F. with said layer of ceramic material fired at between 1600° to 1820°.

7. A composite structure as defined in claim 6 wherein said noble metal halide comprises a chloride of a noble metal selected from the group of noble metals consisting of platinum, palladium, gold and silver.

* * * * *